United States Patent [19]
Lee et al.

[11] Patent Number: 5,273,518
[45] Date of Patent: Dec. 28, 1993

[54] CARDIAC ASSIST APPARATUS

[75] Inventors: Philip H. J. Lee, Woodbury; Michael A. Colson, Minneapolis, both of Minn.

[73] Assignee: Medtronic, Inc., Minneapolis, Minn.

[21] Appl. No.: 829,182

[22] Filed: Jan. 31, 1992

[51] Int. Cl.$^5$ .................................. A61N 1/362
[52] U.S. Cl. .............................. 600/16; 623/3
[58] Field of Search ......................... 600/16-18; 623/3; 128/24.2, 44

[56] References Cited

U.S. PATENT DOCUMENTS

| | | |
|---|---|---|
| 4,245,622 | 1/1981 | Hutchins . |
| 4,411,268 | 10/1983 | Cox . |
| 4,453,537 | 6/1984 | Spitzer ................................ 600/17 |
| 4,573,997 | 3/1986 | Wisman et al. ..................... 623/3 |
| 4,813,952 | 3/1989 | Khalafalla .......................... 600/17 |
| 4,919,661 | 4/1990 | Gibney . |
| 5,007,927 | 4/1991 | Badylak et al. .................... 600/16 |

OTHER PUBLICATIONS

*Transformed Muscle for Cardiac Assist and Repair* by Chiu RC-J, Bourgeois, I. Futura Publishing Company, Inc., Mount Kisco, N.Y. 1990, pp. 255-327.

*Prolonged Circulatory Support By Direct Mechanical Ventricular Assistance*, by G. L. Anstadt, P. Schiff and A. E. Baue, vol. XII Trans. Amer. Soc. Artif. Int. Organs, 1966, pp. 72-79.

*Experimental and Clinical Evaluations of Mechanical Ventricular Assistance* by David B. Skinner, MD. The American Journal of Cardiology, pp. 146-154.

*Sychronously Stimulated Skeletal Muscle Graft for Myocardial Repair* by Dewar, Michael L., et al., Thorac Cardiovasc Surg. 87:325-331, 1984, The Journal of Thoracic and Cardiovascular Surgery, volume 87, No. 3, Mar. 1984, pp. 325-330.

*Myocardial Substitution with a Stimulated Skeletal Muscle: First Successful Clinical Case* by A. Carpentier and J. C. Chachques, The Lancet, Jun. 1, 1985, p. 1267.

*A New Implantable Burst Generator for Skeletal Muscle Aortic Counterpulsation* by Carlos, M., et al., vol. XXXV, Trans. Am. Soc. Artif. Intern. Organs 1989, pp. 405-407.

*Skeletal Muscle-Powered Cardiac Assist Using an Extra-Aortic Balloon Pump* by Neilson, I. R., et al., Biomechanical Cardiac Assist: Cardiomyoplasty and Muscle Powered Devices, Mount Kisco, N.Y., chapter 11, pp. 141-151.

Primary Examiner—Lee S. Cohen
Assistant Examiner—John P. Lacyk
Attorney, Agent, or Firm—Harold R. Patton; Gregory P. Gadson

[57] ABSTRACT

Regulators for improved cardiac assist systems of the type including skeletal muscle powered fluid pressure means, a cardiac cup and/or an aortic balloon pump. The regulators convert the positive pressures generated by contracting muscle into both positive and negative pressures useful in the systems.

10 Claims, 2 Drawing Sheets

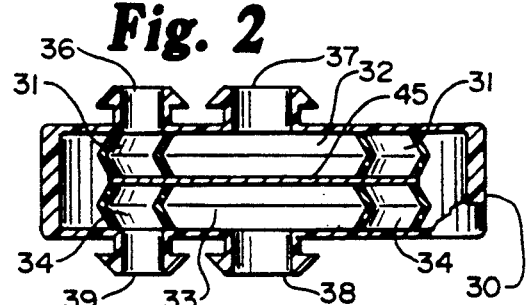
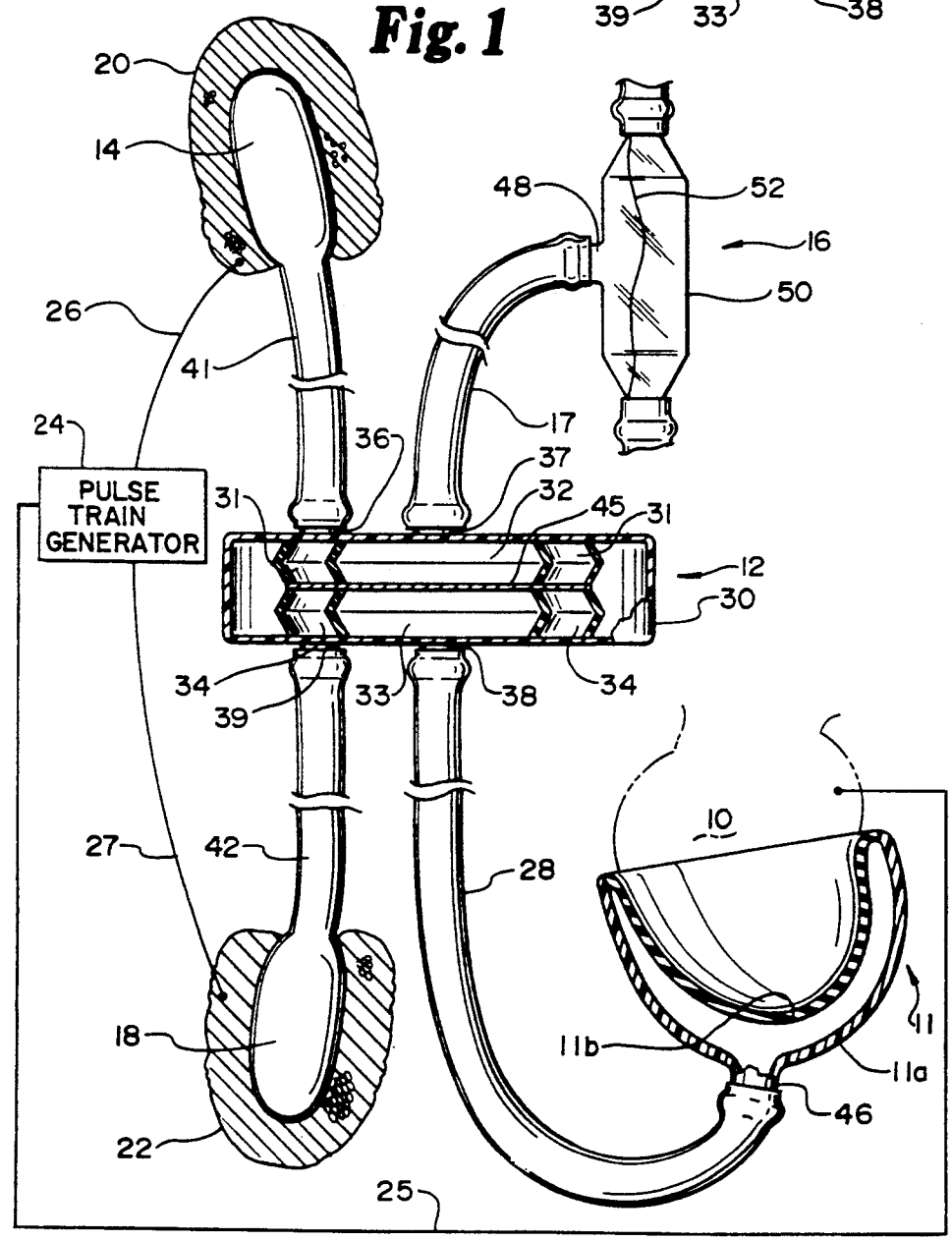

CARDIAC ASSIST APPARATUS

BACKGROUND OF THE INVENTION

1. Field of the Invention

The present invention is related to cardiac assist apparatus, and more particularly, to an improved peri-cardiac implant to assist systole and a peri-aortic device to assist diastole combination in which a regulator of improved design is provided.

2. Description of Related Art

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

Recently there have been developments to provide a cardiac assist cup attached to the heart ventricles and to pump and withdraw air from the cup to assist during systole and diastole, the pulses being coordinated with the rhythm of the heart. This development is described by G. L. Anstadt et al in "Prolonged Circulatory Support by Direct Mechanical Ventricular Assistance", *Trans. ASAIO* 12:72-79 (1966) and D. B. Skinner in "Experimental and Clinical Evaluations of Mechanical Ventricular Assistance", *The American Journal of Cardiology*, 27:146 (1971). Related information is also found in U.S. Pat. No. 4,573,997 to Wisman et al. A broad range of information is available in the book entitled *Transformed Muscle For Cardiac Assist and Repair*, edited by R. Chiu and I. Bourgeois, Futura Publishing Company, Inc. (1990), particularly pp. 255-327.

The principle of the cardiac cup is to provide systolic assist to the heart similar to heart massage. The cup is placed around the sick heart. During systole, the heart is assisted by the diaphragm in the cup which contracts the ventricles. However, it is also necessary to deflate the diaphragm during diastole to allow the heart to receive coronary infusion of blood. This active deflation is viewed as critical for proper assist.

Circulatory counterpulsation with the intra-aortic balloon is now a widely accepted form of cardiac assist. A major limitation is the patient's dependency on an external power source with its risk of infection and restriction in mobility. A totally implantable counterpulsation assist system would offer an important therapeutic option for patients with end-stage heart failure.

Developments have also occurred which utilize a skeletal muscle, which has been transformed to be fatigue resistant, wrapped around the heart in "dynamic cardiomyoplasty", as described in an article by M. L. Dewar et al entitled "Synchronously Stimulated Skeletal Muscle Graft for Myocardial Repair: An Experimental Study", *Journal of Cardiovascular Surgery*, 87:325 (1984). The first successful case was reported by A. Carpentier et al in an article entitled "Myocardial Substitution with a Stimulated Skeletal Muscle: First Successful Clinical Case", *Lancet* 8440:1267 (1985). In dynamic cardiomyoplasty, the latissimus dorsi muscle pedicle is wrapped around the heart, and the muscle is stimulated by an implanted battery-operated, electric pulse device in order to contract the muscle in synchrony with cardiac systole. Also see U.S. Pat. No. 4,919,661 to Gibney. Therefore, advances in technology and skeletal muscle biology now allow for a viable alternative source in cardiac assistance. It has been demonstrated that skeletal muscle can be made fatigue-resistant and powerful enough to continuously assist the heart.

A totally implantable muscle-powered counterpulsation device also has important clinical application. It is useful for patients with chronic heart failure but with some remaining cardiac function. They may or may not be candidates for heart transplantation or artificial heart devices. A muscle powered cardiac assist device has the advantage of not being tethered to an external power source, so that infectious complications are avoided. The development of a new pulse-train (i.e., burst) stimulator that can summate the contraction pattern of a skeletal muscle to make it functionally resemble that of the myocardium and to synchronize it precisely with the selected portion of the cardiac cycle is described in an article by Carlos M. Li et al, entitled "A New Implantable Burst Generator for Skeletal Muscle Power Aortic Counterpulsation", published in *ASAIO Transactions*, July-Sept. 1989, Vol. 35, No. 3, p. 405.

Also known now is the extra-aortic balloon pump of the type disclosed in U.S. Pat. No. 4,245,622 to Hutchins and its equivalent muscle powered pump disclosed in U.S. Pat. No. 4,813,952 to Khalafalla.

In one configuration of a dual chamber extra-aortic balloon pump described by Nielson and Chiu, in the book *Biomechanical Cardiac Assist Cardiomyoplasty and Muscle-Powered Devices*, edited by Ray C. J. Chiu, Futura Publishing Co., Inc., Mount Kisco, 1986 pp. 141-150, a blood pump having a flexible and movable diaphragm is moved by pressure inflating the diaphragm within the pump and is deflated by the normal diastolic vascular pressure. In a counterpulsating fashion, not unlike the function in intra-aortic balloon pumping, the diaphragm is inflated during cardiac diastole and allowed to deflate during systole. The benefit of such action is twofold. Pressure augmentation during diastole infuses the coronaries with extra blood and, thus, oxygen as well as increasing perfusion to the body. Passive pump diaphragm deflation during systole suddenly increases the vascular volume allowing the heart to work against an easier load and so expends less cardiac energy for the amount of blood moved. The net effect is to supply the sick heart with more oxygen during diastole while the heart needs to consume less oxygen in systole for the same blood volume moved. After connecting the balloon to the aorta so that it will be compressed by the latissimus dorsi muscle, the burst stimulator can stimulate the latissimus dorsi muscle during diastole to achieve significant diastolic augmentation. Also see U.S. Pat. No. 4,411,268 to Cox.

To the present time, technical development, when using skeletal muscle as a power source, has only been able to provide positive pressure to the aortic assist counter pulsating blood pump during diastole but there has not been available the means to implement active suction during systole. Similarly, with the cardiac cup, both positive and then negative pressure are required for ideal operation. This invention provides the means for such regulation to meet this need.

SUMMARY OF THE INVENTION

It is a purpose of the present invention to provide cardiac assist systems of various embodiments which are totally implanted corporeally.

It is a purpose of the present invention to provide improvements in known systems which make use of muscle powered peri-cardiac cup copulsation devices and aortic balloon pumps which are skeletal muscle powered.

It is a further aim of the present invention to provide an improved pressure conversion regulator for coordinating the cardiac assist copulsation and counterpulsation devices.

An improved system in accordance with the present invention comprises a copulsation and a counterpulsation cardiac assist device wherein the copulsation means includes an extra-ventricular assist means including a fluid expansible envelope for compressing the heart during systole and the counterpulsation means comprises an aortic pump means including a fluid expansible balloon for moving blood in the aorta during diastole. Muscle powered fluid pressure means are provided for supplying alternating fluid pressure to the copulsation means and to the counterpulsation means. Means are provided for sensing the heart rate and means for producing an electric pulse to the selected muscles to contract the respective muscles in response to signals from the means for detecting the heart rate for producing the required alternating fluid pressure flow.

The improved regulative device used with this system is designed to provide both positive and negative pressures in response to the alternating positive pressures provided by the muscle powered fluid pressure means. It is a four-chamber device in which the first chamber is toroidal in configuration and encircles a second chamber positioned within the open center of the toroidal first chamber. The two chambers sit on a rigid plate which in turn sits on a second set of chambers similar to the first set. The four chambers are resilient and elastic fluid pressure chambers having an independent port opening into each chamber. The ports are variously connected to the muscle powered fluid pressure means, the peri-cardiac cup and the aortic pump such that when fluid pressure is applied during systole and diastole the regulator device provides not only positive pressure but negative pressure as well to enhance withdrawal of the fluid from a respective one of the copulsation means and counterpulsation means.

In a more specific embodiment of the present invention, the regulative device includes an implantable housing defining a cavity of circular cylindrical outline having a rigid plate positioned between upper and lower sets of chambers, the chambers being expansible and contractible within the confines of the housing.

Primary advantages of the unique regulator design are:

simplicity—it can be manufactured with presently available materials;

little frictional loss—no mechanical pivot points;

chamber geometry—translates outer balloon inflation to inner chamber suction;

flat cylindrical design—functions better than a long cylindrical design. It is believed, therefore, that preferred embodiments of the regulator will have a larger diameter dimension than h eight dimension.

positive pressure transformed to negative pressure—a rigid plate keeps the inner chamber(s) inflation controlled and enables suction to occur; and shape—shape for fixation to the spine or ribcage.

In a more specific embodiment of the system improved by the present invention, the extra-ventricular envelope is in the form of a peri-cardiac cup. The pressurized fluid to the cup originates in a balloon pump provided under the latissimus dorsi muscle or wrapped by the muscle so that it can be compressed by the muscle when the muscle is contracted as a result of a stimulus from the burst stimulator during systole. The extra-aortic (peri-aortic) pump means includes a fluid expandable balloon extending on an exterior wall of the aorta adapted to compress a portion of the aorta, and a balloon pump compressed by the other latissimus dorsi muscle so that it can be compressed by the muscle and the muscle is contracted as a result of stimulus from the burst stimulator during diastole.

A totally implantable system is provided wherein the ventricular cup and the extra-aortic pump are coordinated to provide the maximum assist to the heart during both systole and diastole and a negative pressure assist is provided by a regulator of improved design for evacuating the cup and/or aortic jacket during diastole and systole, respectively. In one embodiment in which the extra-aortic pump is a jacket, the cardiac assist system is completely isolated from the blood circulation through the aorta and the heart in order to avoid complications from the blood circulation being in contact with synthetic objects.

In broad aspect, the system described above provides a cardiac assist system comprising copulsation means for compressing a portion of the heart during systole and decompression during diastole; counterpulsation means for compressing a portion of the aorta during diastole and decompressing during systole; fluid pressure means couples to said copulsation means and to said counterpulsation means, for alternately supplying fluid pressure thereto; said fluid pressure means being in fluid pressure communication with at least two selected body muscles; sensor means for sensing the heart and for generating sensing signals; and means responsive to said sensing signals for generating stimulation pulses to said selected muscles.

In still another broad aspect, the system described above provides a method of assisting systole and diastole comprising effecting compression of a portion of the heart during systole and decompression during diastole, by copulsation means; effecting movement of blood volume in the aorta during diastole and decompression during systole, by counterpulsation means; alternately supplying fluid pressure to said copulsation and counterpulsation means, said fluid pressure communicating with at least two selected body muscles; sensing the heart and generating a sensing signal; and generating stimulation pulses to said selected muscles.

In another embodiment of the improved regulator of the invention only three chambers are used, omitting the fourth chamber i.e. having only a single chamber on one side of the rigid plate.

This embodiment has particular use in a new system in which a ventricular cup or an extra-aortic jacket is operated from the second chamber by alternating pressure applied to the first and third chambers by means of muscle powered fluid means.

In all embodiments the fluid may be a gas or liquid, preferably air or water or a mixture of the two.

BRIEF DESCRIPTION OF THE DRAWINGS

FIG. 1 is a fragmentary, partly diagrammatic view of details of one embodiment of the present invention showing a 4 chamber regulator;

FIG. 2 is a side view in partial cross-section of the regulator of FIG. 1;

DESCRIPTION OF THE PREFERRED EMBODIMENTS

Figure 4:
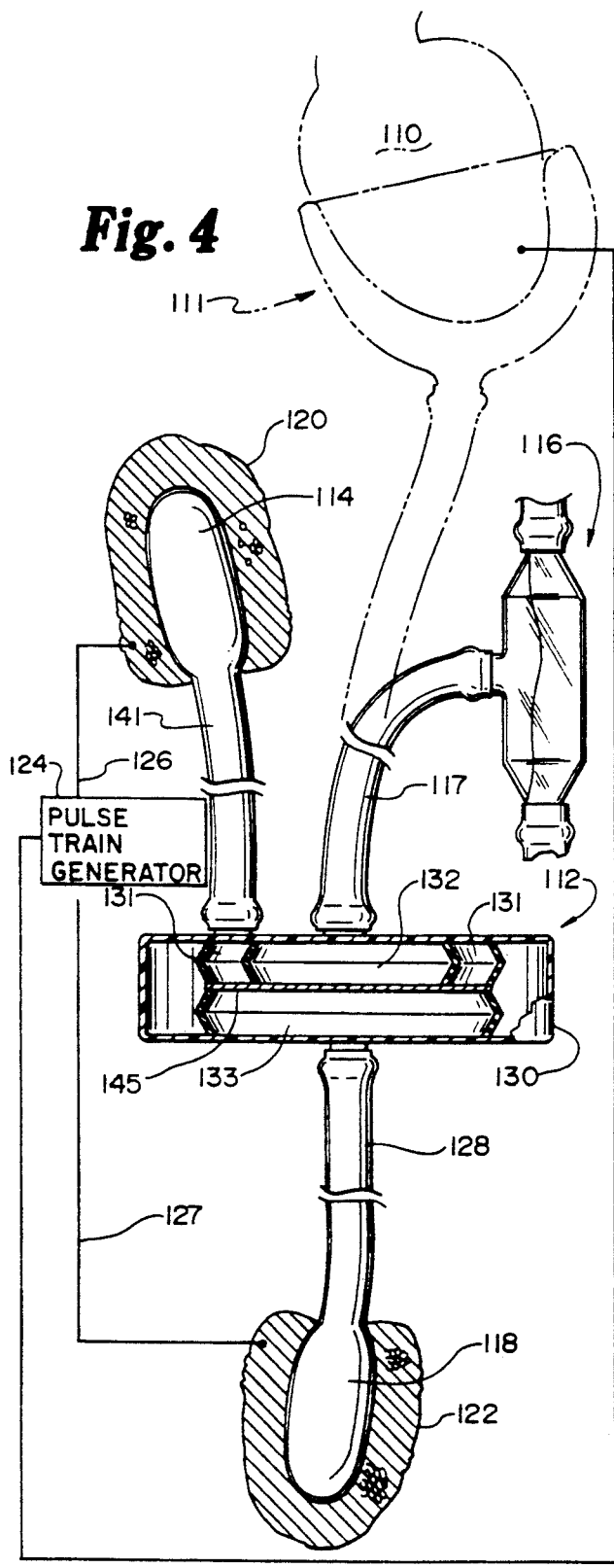
FIG. 4 is a diagram of a system which makes use of the 3 chamber regulator embodiment of the invention.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

Figure 3:
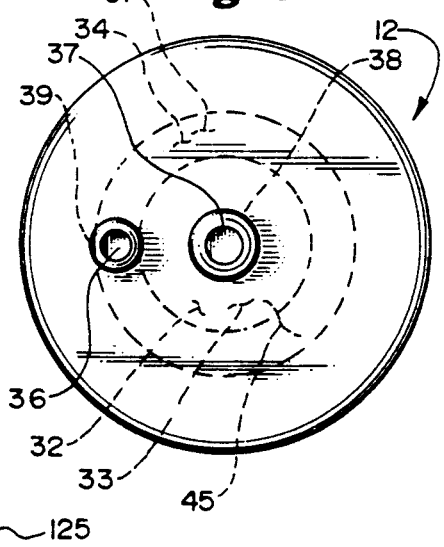
FIG. 3 is a top view of the regulator of FIG. 2.

Referring now to FIGS. 1, 2 and 3 of the drawings, there is shown an embodiment of the present invention which provides a system comprising, among other things, in combination the body of a patient (not shown), namely the thoracic cage, the heart 10, and a ventricle cup 11 or other hemodynamic assist devices placed on the heart. As shown in FIG. 1, a regulator 12, which will be described further, is included and is adapted to be located in a natural cavity of the human body, e.g., in the abdomen or the chest. Also part of the system, as shown in FIG. 1, is an aortic pump generally indicated at 16 which communicates with the regulator 12 by means of conduit 17.

A pair of fluid balloons 14 and 18 are located in association with skeletal muscles, such as the latissimus dorsi muscles 20 and 22, respectively. Finally, a pulse train generator 24 is also located in part of the body with electrical leads 26 and 27 to each muscle 20 and 22 and a sensor lead 25 attached to heart 10.

Cup 11 has a construction such as described in the Anstadt article previously referred to and which is herein incorporated by reference.

The Skinner article is also herewith incorporated by reference as describing a typical ventricular cup suitable for use in the present invention. Also U.S. Pat. No. 4,573,997 and the book *Transformed Muscle For Cardiac Assist and Repair* are likewise incorporated by reference. Cup 11 includes a relatively inextensible outer envelope 11a with a liner 11b of flexible material. A flexible fluid conduit 28 extends from an inlet port 46 of cup 11, to port 38 on regulator 12.

Regulator 12, in accordance with the embodiment shown herein, is in the form of a circular cylinder shell or housing 30 of a hard implantable grade polymer or titanium similar to the shells of pacemakers. Housing 30 is depicted as cylindrical for purposes of illustration, although it is not necessarily limited to a cylinder shape. It should, however, be relatively flat. Housing 30 contains four separate chambers; a first chamber 31 of toroidal configuration, a second chamber 32 encircled by chamber 31 and in the open center thereof, a third chamber 33, and a fourth chamber 34, which is also toroidal in configuration and similar to chamber 31. Chamber 33 is likewise similar in position and configuration to chamber 32. There are four ports 36, 37, 38 and 39 from respective chambers 31, 32, 33 and 34. Port 36 and port 39 communicate through conduits 41 and 42 to respective balloons 14 and 18 located underneath or wrapped by respective latissimus dorsi muscles 20 and 22, respectively. All conduits are preferably implantable grade reinforced silicone or other polymer material.

Inside housing 30, as already noted, are two toroidal chambers (donut shaped) 31 and 34 lying one over the other. The inner spaces define and form chambers 32 and 33 respectively. Each chamber is separate and sealed from the others. A thin rigid plate 45, metal or plastic preferably or other composite material, separates chambers 31, 32 from 33, 34 as illustrated. That is, chambers 31, 32 contact the upper surface of plate 45 and are received or seated thereon while chambers 33, 34 contact the lower opposite surface of plate 45 and are received or seated thereon. As can be seen, plate 45 "floats" between the upper chambers 31, 32 and the lower chambers 33, 34 by being "sandwiched" therebetween. The walls of the chambers are of a resilient elastic material, preferably butyl rubber as it has the ability of withstanding high pressures (in this case on the order of 200 mm Hg.) and excellent resilience to repeated stretching. The rubber should be reinforced with webbing which provides an absolute stretch limit on the chamber walls. A bellows configuration (as shown in FIGS. 1, 2, 3) for the chamber walls or a balloon configuration may be used. A bellows configuration, however, requires rigid reinforcement in the walls.

In operation, chambers 31, 32 in the extremes are either nearly deflated or totally expanded. If chambers 31, 32 are fully expanded, chambers 33, 34 are deflated and vice versa. More specifically, when muscle 20 contracts causing chamber 31 to expand by the increase in fluid pressure from balloon 14, chamber 32 also expands. Surprisingly, this causes a negative pressure in chamber 32 causing aortic pump diaphragm 52 to deflate. At the same time, chambers 33, 34 decrease in volume causing re-inflation of the balloon 18 thereby preloading muscle 22 and re-inflation of the cardiac cup diaphragm 11b to thereby assist in heart systole.

In the next cycle, the opposite occurs with chambers 33, 34 increasing in volume. Suction occurs at chamber 33 causing the cardiac cup to actively deflate. The same volume is pumped from chamber 32 to re-inflate aortic pump 16.

In an application of the aortic pump (not shown) jacket 16 can be stitched or otherwise fastened to the vertebrae and balloon 2 extends between the outer inextensible housing 50 and the aorta. Flexible tube 17 extends between inlet port 48 on balloon 52, and port 37 communicating with chamber 32 in regulator 12.

A balloon 18 is provided just under the latissimus dorsi muscle 22 which is placed between the muscle and the ribs. Balloon 18 communicates with chamber 34 by means of tube 42 extending to port 39.

The pulse train generator 24 is of the type having a burst or a series of signals as a pulse train as is described in the Li et al article referred to above. A suitable pulse train generator 24 is capable of sensing the rate of the heart and includes a sensor/pacing lead 25. As the rhythm of the heart changes, the sensor logic within pulse train generator 24 will vary the rate of the discharge of the pulses to the respective muscles 20 and 22. A memory chip within the pulse train generator 24 can be modified or reprogrammed by telemetry. There are leads 26 and 27 to each muscle 20 and 22 respectively for providing the necessary muscle stimulant in order to contract these muscles.

In the embodiment of FIGS. 1-3, the design of the system and regulator 12 controls when cardiac cup 11 is deflated and aortic jacket 16 is inflated and vice-versa. They should not be initially set so as to both be inflated or deflated at the same time. Similarly, when one balloon is compressed, the other is inflated and vice-versa.

The design of the regulator allows flexibility and there are opportunities for fine-tuning and optimization.

When chambers 31, 34 are fully expanded, they should be substantially the same volume. The fully extended volume for chambers 32, 33 can be different than for chambers 31, 34. More volume at chambers 32, 33 can be moved by physically increasing them by design, but this increase in volume is at the expense of mechanical advantage. The design of the regulator must be such that, when chamber 31 or chamber 34 are fully expanded, chambers 32 and 33, respectively, move the appropriate volumes.

In operation activity of heart 10 is sensed by pulse train generator 24, and, when the heart is about to start a cycle at systole, the pulse train generator 24 will selectively send a signal through lead 26 to the latissimus dorsi muscle 20 so that it can contract and compress balloon 14. The fluid from balloon 14 then travels through the tube 41 to expand chamber 31 in regulator 12. Chamber 32 also expands, creating suction in conduit 17 and deflating aortic pump diaphragm 52. At the same time, chambers 33, 34 decrease the volume and the fluid therein is forced through ports 38 and 39, respectively. The resultant positive pressure in conduit 28 to cup 11 expands the envelope 11a, 11b and thus presses the cup diaphragm 11b against the ventricle and assists the heart by compressing it during systole. Also at the same time, the positive pressure in conduit 42 fills balloon 18. Immediately thereafter, the latissimus dorsi muscle 20 relaxes and at the same time a signal is provided from the pulse train generator 24 to the latissimus dorsi muscle 22, thereby contracting balloon 18 and forcing the fluid out of balloon 18 through the tube 42 into chamber 34. As the fluid flow passes into chamber 34, it causes chamber 33 to expand and compresses chambers 31, 32. Expansion of chamber 33 creates negative pressure or suction at port 38 and in conduit 28, thus drawing the fluid from conduit 28 and thus from the cup 11. Due to compression chamber 31 fluid is forced to expand balloon 20 and compression of chamber 32 inflates aortic pump 16. The cycle is repeated. Thus, every time a latissimus dorsi muscle 20 or 22 is contracted, the other of the muscle 20 or 22 is allowed to relax.

When the cycle is reversed, of course, fluid pressure again goes to cup 11 surrounding the heart 10 to assist systole, and aorta pump diaphragm 52 is allowed to collapse by the fluid being entrained back to the chamber 32 by way of conduit 17. The latissimus dorsi muscles 20 and 22 are, by means of the pulse train generator, caused to operate alternatively between contraction and thus compression against the respective bellows and relaxation.

In a further embodiment of the regulator of the invention, there is shown in FIG. 4 a three-chamber regulator generally indicated at 112 and a novel system incorporating it. Regulator 112 allows the full force of the muscle to be applied to a cardiac cup 111 or to an aortic blood pump 116. In this system, two latissimus dorsi muscles 120 and 122, respectively, are connected to balloons 114 and 118 as shown, balloon 114 being connected to a first chamber 131 of toroidal configuration. A second chamber 132 is encircled in the center opening as in the previous embodiment and is connected to either a cardiac cup 111 or an aortic blood pump 116, optionally. Balloon 118 is connected to a third chamber 133. Similar to the previous embodiment, chambers 131, 132 are received on the upper surface of a rigid plate 145 while the single lower chamber 133 is received on the opposite surface of the plate.

In this system, instead of dissipating energy partially to the cardiac cup side and partially to the aortic jacket side during the contraction of one muscle as in the system of FIGS. 1-3, most of the energy of one muscle contraction in one cycle is used to power one assist device, either a cardiac cup 111 or an aortic blood pump 116. Then, in the next cycle, the full contraction of the other muscle is used to actively suction the one assist device.

It should be noted that there is a mismatch in chamber volumes 131 and 133. If this mismatch is not desirable (in some cases it may be beneficial), then chamber 133 may be made smaller. Also, balloon 118 might be made larger in relation to balloon 114.

The operation of the system in which the aortic blood pump is connected with regulator in FIG. 4 is as follows: Heart 110 is sensed by pulse train generator 124. When heart 110 is about to start a cycle at systole, the pulse train generator 124 selectively sends a signal through lead 126 to the latissimus dorsi muscle 120 so that it can contract and compress balloon 114. The fluid from balloon 114 then travels through conduit 141 to expand chamber 131 causing suction in expanding chamber 132 and compression of chamber 133. The suction in chamber 132 deflates the diaphragm in aortic pump 116 "unloading" the heart. At the same time, compression chamber 133 causes fluid to flow to balloon 118 causing it to expand. Immediately thereafter the muscle 120 relaxes and at the same time a signal is provided from the pulse train generator 124 to the latissimus dorsi muscle 122, thereby contracting balloon 118 and forcing the fluid out of balloon 118 through conduit 128 into chamber 133 to expand chamber 133, causing compression of chambers 131 and 132. This compression causes fluid to fill balloon 114 and to inflate the aortic pump 116, forcing blood toward the heart or coronaries during diastole. The cycle is repeated. Thus, every time a latissimus dorsi muscle 120 or 122 is contracted, the other of the muscle 120 or 122 is allowed to relax.

The invention has been particularly described by reference to the use of the muscles latissimus dorsi. However, other muscles can also be exploited in carrying out the invention, for example, the pectoralis major, the rectus or serratus may be utilized. Also, the regulator is intended primarily for cardiac assist applications, but its attributes may be amenable to other applications and this invention is intended to cover them as well.

This completes the description of the preferred and alternate embodiments of the invention. Those skilled in the art may recognize other equivalents to the specific embodiment described herein which equivalents are intended to be encompassed by the claims attached hereto.

What is claimed is:

1. In a cardiac assist system including:
   first fluid pressure responsive means, herein termed a peri-cardiac assist means, for compressing a portion of a heart during systole and decompressing it during diastole;
   second fluid pressure responsive means, herein termed a peri-aortic jacket means, for moving blood volume in the aorta of the heart during diastole and suddenly increasing vascular space during systole to "unload" the heart;
   first and second fluid pressure supply means coupled respectively to the first and second fluid pressure responsive means for alternatively supplying fluid pressure thereto, each of the fluid pressure supply means being adapted for fluid pressure communication with different selected body muscle, respectively;

pressure regulator means for generating positive and negative pressures operatively interconnected with the fluid pressure supply means and the fluid pressure responsive means;

sensor means adapted for sensing the heart and for generating sensing signals; and means responsive to the sensing signals for generating stimulation pulses to the selected muscles, the improvement comprising said pressure regulator means coupled between said first fluid pressure supply means and said first fluid pressure responsive means, and coupled between said second fluid pressure supply means and said second fluid pressure responsive means, said pressure regulator means comprising a multi-chamber assembly including:

a first closed fluid pressure chamber of toroidal configuration having an open center;

a second closed fluid pressure chamber positioned within the open center thereof and encircled by the first chamber;

a rigid plate receiving said first and second chambers on a surface thereof;

third and fourth closed fluid pressure chambers, the third being positioned within the open center of and encircled by the fourth which is of toroidal configuration, the third and fourth chambers being received on a surface of the rigid plate opposite to the surface receiving the first and second chambers;

all four fluid pressure chambers are formed of a flexible elastic material adapted for interacting with the fluid supplied by the first and second fluid pressure supply means, and means operatively supporting the multi-chamber assembly for expansion and contraction;

individual ports opening into each of the four fluid pressure chambers, and fluid pressure conduit means connecting the first chamber by means of its port to the first fluid pressure supply means, fluid pressure conduit means connecting the second chamber by means of its port to the peri-cardiac assist means;

fluid pressure conduit means connecting the third chamber by means of its port to the peri-aortic jacket means and fluid pressure conduit means connecting the fourth chamber by means of its port to the second fluid pressure supply means whereby: the application of fluid pressure to the first chamber at diastole causes expansion of both the first chamber and second chamber, movement of the plate against the third and fourth chambers and contraction thereof, resulting in the compression of the third and fourth chambers and a negative suction pressure in the second chamber and consequently in the peri-cardiac assist means; at the same time the peri-aortic jacket means is inflated; and the alternate application of fluid pressure to the fourth chamber at systole causes expansion of the fourth chamber and the third chamber, movement of the plate against the first and second chambers and contraction thereof, resulting in compression of the first and second chambers and a negative suction pressure in the third chamber and consequently in the peri-aortic jacket means and at the same time the peri-cardiac assist means is inflated.

2. A cardiac assist apparatus comprising peri-cardiac assist means including a fluid expansible envelope for compressing a heart during systole, peri-aortic jacket means including a fluid expansible aortic blood pump means moving blood volume during diastole first and second muscle powered fluid pressure means for supplying fluid pressure alternately to the peri-cardiac assist means and to the aortic pump means, respectively, means for sensing the heart rate, means for producing a stimulating pulse to the muscle powered fluid pressure means to contract the muscle thereof in response to the heart rate for producing the alternating fluid pressure flow, and pressure control means for controlling the alternating fluid pressure flow and generating therewith a negative pressure to alternately enhance withdrawal of the fluid from a respective one of the peri-cardiac assist means and the aortic pump means, and a pressure controlling means comprising a multi-chamber assembly including:

a first closed fluid pressure chamber of toroidal configuration having an open center;

a second closed fluid pressure chamber positioned within the open center thereof and encircled by the first chamber;

a rigid plate receiving said first and second chambers on a surface thereof;

third and fourth closed fluid pressure chambers, the third being positioned within the open center of and encircled by the fourth which is of toroidal configuration, the third and fourth chambers being received on a surface of the rigid plate opposite to the surface receiving the first and second chambers;

all four fluid pressure chambers are formed of a flexible elastic material adapted for interacting with the fluid supplied by the first and second fluid pressure supply means, and means operatively supporting the multi-chamber assembly for expansion and contraction;

individual ports opening into each of the four fluid pressure chambers, and fluid pressure conduit means connecting the first chamber by means of its port to the first fluid pressure supply means, fluid pressure conduit means connecting the second chamber by means of its port to the peri-cardiac assist means, fluid pressure conduit means connecting the third chamber by means of its port to the peri-aortic jacket means and fluid pressure conduit means connecting the fourth chamber by means of its port to the second fluid pressure supply means whereby the application of fluid pressure to the first chamber at diastole causes expansion of both the first chamber and second chamber, movement of the plate against the third and fourth chambers and contraction thereof, resulting in the compression of the third and fourth chambers and a negative suction pressure in the second chamber and consequently in the peri-cardiac assist means at the same time the aortic pump means is inflated and pressure to the fourth chamber at systole causes expansion of the fourth chamber and the third chamber, movement of the plate against the first and second chambers and contraction thereof, resulting in the compression of the first and second chambers and a negative suction pressure in the third chamber and consequently in the aortic pump means.

3. A regulator for converting successive positive pressures to alternating positive and negative pressures, comprising
a multi-chamber assembly including:
a first closed fluid pressure chamber of toroidal configuration having an open center;
a second closed fluid pressure chamber positioned within the open center of and encircled by the first chamber;
a rigid plate receiving said first and second chambers on a surface thereof;
a third closed fluid pressure chamber received by rigid plate on a surface opposite to the surface receiving the first and second chambers, and
in which all three fluid pressure chambers are formed of a flexible elastic material adapted for interacting with a fluid medium therein, and
means operatively supporting the multi-chamber assembly for expansion and contraction, and
a separate port opening into each fluid pressure chamber for providing the ingress and egress of a fluid medium to each chamber whereby the application of fluid medium pressure to the port of the first chamber causes expansion of the first chamber and second chamber, movement of the plate against the third chamber and contraction of third chamber resulting in the production of a suction pressure within the second chamber and positive output compressive pressure within the third chamber, and whereby the application of fluid pressure into the third chamber causes expansion of the third chamber, movement of the plate against the first and second chambers resulting in contraction of the first and second chambers and in the production of a positive compressive pressure leaving the ports of each of the first and second chambers.

4. The regulator of claim 3 wherein the supporting means includes a housing and said ports adapted for implantation.

5. The regulator of claim 3 including a fourth fluid pressure chamber, the fourth chamber being of toroidal configuration and encircling the third chamber in a manner similar to the arrangement of the first and second chambers, the fourth chamber also being received on the opposite surface of the rigid plate and including a separate port opening into the chamber.

6. The regulator of claim 5 wherein the supporting means includes a housing adapted for implantation.

7. A cardiac assist system comprising:
a regulator for converting successive positive pressures to alternating positive and negative pressures, comprising a multi-chamber assembly including:
a first closed fluid pressure chamber of toroidal configuration having an open center;
a second closed fluid pressure chamber positioned within the open center of and encircled by the first chamber;
a rigid plate receiving said first and second chambers on a surface thereof;
a third closed fluid pressure chamber received by rigid plate on a surface opposite to the surface receiving the first and second chambers, and
in which all three fluid pressure chambers are formed of a flexible elastic material adapted for interacting with a fluid medium therein, and
means operatively supporting the multi-chamber assembly for expansion and contraction, and
a separate port opening into each fluid pressure chamber for providing the ingress and egress of a fluid medium to each chamber whereby the application of fluid medium pressure to the port of the first chamber causes expansion of the first chamber and second chamber, movement of the plate against the third chamber and contraction of third chamber resulting in the production of a suction pressure within the second chamber and positive compressive pressure within the third chamber, and whereby the application of fluid pressure into the third chamber causes expansion of the third chamber, movement of the plate against the first and second chambers resulting in contraction of the first and second chambers and in the production of a positive compressive pressure leaving the ports of each of the first and second chambers;
fluid pressure responsive means for compressing and decompressing a hemodynamic assist device placed in a predetermined position of an anatomy, fluid pressure responsive means being in fluid communication with the second chamber of the regulator;
first fluid pressure supply means in fluid communication with the first chamber for supplying fluid pressure thereto, the first fluid pressure supply means being adapted for interaction with a selected body muscle;
second fluid pressure supply means in fluid communication with the third chamber for supplying fluid pressure thereto, the second fluid pressure supply means being adapted for interaction with a different selected body muscle;
sensor means for sensing a heart and for generating sensing signals, and
means responsive to the sensing signals for generating stimulation pulses to the selected muscles.

8. The system of claim 7 in which the fluid pressure responsive means is a cardiac cup.

9. The system of claim 7 in which the fluid pressure responsive means is an aortic blood pump.

10. The system of claim 7 in which the fluid pressure response means is an extra-aortic jacket.

* * * * *